United States Patent [19]

Kuhlmann et al.

[11] Patent Number: 5,498,546
[45] Date of Patent: Mar. 12, 1996

[54] WASHING PROCESS

[75] Inventors: Werner Kuhlmann, Monheim; Hans-Willi Kling, Wuppertal, both of Germany

[73] Assignee: Henkel Kommanditgesellschaft auf Aktien, Duesseldorf, Germany

[21] Appl. No.: 392,757

[22] PCT Filed: Aug. 16, 1993

[86] PCT No.: PCT/EP93/02170

§ 371 Date: Feb. 24, 1995

§ 102(e) Date: Feb. 24, 1995

[87] PCT Pub. No.: WO94/4741

PCT Pub. Date: Mar. 3, 1994

[30] Foreign Application Priority Data

Aug. 24, 1992 [DE] Germany .............. 42 28 021.4

[51] Int. Cl.$^6$ .......... G01N 31/00; G01N 33/00; G01N 35/08; G01N 1/00
[52] U.S. Cl. .............. 436/55; 436/52; 436/164; 436/175; 252/174.17; 252/DIG. 1; 252/DIG. 14; 252/408.1
[58] Field of Search .......... 252/174.17, DIG. 1, 252/DIG. 14, 408.1; 436/55, 52, 164, 175

[56] References Cited

U.S. PATENT DOCUMENTS

| | | | |
|---|---|---|---|
| 2,408,900 | 10/1946 | Alston et al. | 436/52 |
| 2,975,136 | 3/1961 | Thomas et al. | 252/51.5 |
| 4,282,001 | 8/1981 | Klose et al. | 23/230 B |
| 4,695,292 | 9/1987 | Osborg | 44/64 |
| 4,900,512 | 2/1990 | Meyrat et al. | 422/63 |
| 5,057,303 | 10/1991 | Casey | 252/408.1 |
| 5,196,169 | 3/1993 | Schick et al. | 422/81 |
| 5,252,486 | 10/1993 | O'Lear et al. | 436/52 |

FOREIGN PATENT DOCUMENTS

| | | | |
|---|---|---|---|
| 2543352 | 4/1977 | Germany | G01N 33/18 |
| 2949254 | 6/1981 | Germany | D06F 37/42 |
| 9209568 | 6/1992 | WIPO | C07C 281/02 |

*Primary Examiner*—Christine Skane
*Assistant Examiner*—Patricia Hailey
*Attorney, Agent, or Firm*—Ernest G. Szoke; Wayne C. Jaeschke; Real J. Grandmaison

[57] ABSTRACT

A process for determining the concentration of washing-active substances in a wash liquor involving the steps of:

(a) preparing a wash liquor containing washing-active substances;

(b) adding a reducing sugar to the wash liquor in an amount proportional to the washing-active substances present in the wash liquor; and (c) measuring the content of reducing sugar present in the wash liquor.

10 Claims, No Drawings

WASHING PROCESS

BACKGROUND OF THE INVENTION

1. Field of the Invention

This invention relates to a washing process in which the concentration of the wash liquor is determined by analysis.

2. Discussion of Related Art

In the machine washing of laundry, it is desirable, above all in the institutional sector, completely or partly to automate dosage of the detergent in the preparation or regeneration of the wash liquor. To control dosage according to requirements, it has proved to be useful to employ not only external parameters, but also the actual concentration of washing-active substance in the liquor as a guide for subsequent dosage of the detergent. The necessary dosage is thus the difference between the required concentration and actual concentration of washing-active substance. Control methods such as these are today mainly used in batch washing machines, the fact that the total conductivity of the liquor increases with increasing concentration being used to determine the content of washing-active substance in the liquor. The connection between conductivity and concentration of washing-active substances has to be empirically determined for each new composition of a detergent. With this system, difficulties arise out of the highly variable input of electrolytes with the soiled washing which leads to inaccurate analysis results and hence to incorrect dosage. In addition, DE-OS 29 49 254 describes a process in which the concentration of wash liquors and cleaning solutions is photometrically determined through the content of fluorescent dyes. The disadvantage of this process lies in the tendency of all dyes to be adsorbed onto textile fibers from solution so that the wash liquor loses these dyes more quickly than the other active substances. Since, in addition, dye adsorption also depends on the quality of the fibre material, the concentration of washing-active substances cannot be reliably determined in this way. Accordingly, for more reliable dosage of the detergent, efforts have long been made to find a process which would not be affected by such factors.

DESCRIPTION OF THE INVENTION

A correspondingly improved process has now been found.

The present invention relates to a washing process using an aqueous solution of washing-active substance, in which the concentration of washing-active substance in the solution is indirectly determined by determining the content of a reducing sugar which is added during preparation of the wash liquor in a quantity proportional to the quantity of washing-active substance. In a preferred embodiment, the sugar has been added in a certain constant ratio to the washing-active substance or to the mixture of several washing-active substances, i.e. the detergent, before preparation of the actual wash liquor.

In the context of the present application, washing active substances are principally surfactants and builders, but also for example redeposition inhibitors, bleaching agents, enzymes, detergency boosters and antimicrobial agents.

Glucose is preferably used as the reducing sugar.

The use of a reducing sugar as a tracer not only solves the problems of known concentration measuring processes, because reducing sugars are neither carried over into the wash liquor nor adsorbed onto textile fibers in significant amounts, it also affords unexpected advantages in the analysis itself. Thus, it has been found that these compounds can be determined largely independently of the other detergent ingredients in the wash liquor and that their determination can be completed so quickly that the result may be used to control ongoing processes. In addition, sugars are biodegradable and toxicologically safe and do not affect the washing process.

The quantity of sugar which has to be added to the wash liquor depends primarily on the sensitivity with which the compound used can safely be analytically determined under these conditions. The quantity to be selected does of course also depend to a large extent on the analysis technique. In the case of the reducing sugars used in accordance with the invention, the in-use concentrations are typically between about 0.02 and 2 g/l wash liquor and preferably between about 0.1 and about 1 g/l wash liquor. If the reducing sugars are directly incorporated in the detergent from which the wash liquor is prepared, the detergent contains around 1 to 20% by weight and preferably 3 to 10% by weight of reducing sugar in addition to at least one surfactant and at least one builder. If the wash liquor is not prepared from a single detergent which contains all the components required for washing, but instead is prepared by addition of individual active substances or combinations of active substances to which the reducing sugar is added beforehand, the active substances or mixtures will contain correspondingly more reducing sugar.

The analysis method by which the content of sugar in the wash liquor is determined may be freely selected within virtually any limits and adapted to the conditions of the washing process. Preferred analysis methods are sensitive methods which manage with minimal sugar contents and fast, continuous methods. Accordingly, photometric determination of the sugar content after a color-forming reaction between the tracer and an added reagent is particularly preferred. The color-forming reaction may be carried out on individual samples of the wash liquor to be analyzed, leading after photometry to corresponding individual results. However, concentration may also be continuously monitored by carrying out the reaction between tracer and reagent continuously in a stream branched off from the wash liquor, the technique known as flow injection analysis having proved to be particularly effective in this regard. In flow injection analysis, an equivalent stream of one or more reagents is added to the sidestream of solution to be analyzed, optionally after suitable pretreatment, such as filtration or temperature control, the combined stream—after appropriate mixing—is subjected, if necessary continuously, to other measures, such as heating for example, until the required color reaction is complete and the solution can be delivered to a photometric measuring cell. Typical flow rates for these solutions are of the order of 0.1 to 2.5 ml per minute. The reading obtained after a certain delay is always an indication of the particular tracer concentration present which enables the concentration of the liquor to be continuously monitored. The fully continuous mode of operation may be replaced with equal effect by the periodic determination of individual samples by flow injection analysis which can also be carried out automatically.

Aromatic hydrazine compounds, for example 4-aminobenzhydrazide, have proved to be suitable color-forming reagents for the reducing sugars, particularly glucose, used as tracers in accordance with the invention. With the reducing sugars, particularly glucose, these aromatic hydrazine compounds form particularly bright yellow colored hydrazones which are easy to detect by photometry. This reaction is known from the literature for the analytical detection of sugars so that there is no need here for a more detailed description of the reaction conditions. It is remarkable that this color reaction of the sugars takes place very largely independently of the other constituents of the detergent.

The process according to the invention may be used with advantage anywhere where the active substance content of a wash liquor has to be subsequently determined. This is the case above all in the institutional sector where one and the same wash liquor is often used for several washing processes during which the concentration of washing-active substance can be uncontrollably reduced by various factors, for example by the introduction of relatively dilute liquors or water or by the removal of concentrated liquor with the washing. To return the wash liquor to the required concentration, the actual content of active substance can be determined by the method according to the invention and detergent subsequently introduced in a quantity corresponding to the result obtained. Because the process according to the invention can be carried out automatically or substantially automatically, it is particularly suitable for the more or less automatic control of detergent dosage which is now required in the preparation or regeneration of wash liquors in institutional laundries.

EXAMPLE

Hospital laundry was washed under the following conditions in a 13-compartment batch washing machine installation operated continuously in countercurrent:

| Run-through time: | 30 minutes |
|---|---|
| Cycle time: | 138 seconds |
| Load: | 35 kg per compartment |
| Liquor ratio: | 1:5 |
| Detergent concentration (required) | |
| -in compartment 1: | 2.8 g/l |
| -in compartment 5: | 1.4 g/l |

The powder-form detergent used contained silicate and soda as builders and alkyl benzenesulfonate, fatty alcohol ethoxylate and soap as surfactants and also 5.00% by weight of glucose as tracer. The concentration of detergent in the liquor in compartment 1 and compartment 5 was determined by bypass control and by the analysis method according to the invention and was controlled by comparison of the programmed set values with the actual values determined using a microprocessor.

In another case, automatic control of detergent dosage was only carried out in compartment 5, conventional time/quantity-dependent dosage being used in compartment 1.

The apparatus used for analysis was made up of standard units connected by Teflon hoses (internal diameter 0.5 mm). The following solutions were used:

Solution 1: 2.5 g of 4-aminobenzhydrazide and 12 g of NaOH in 150 ml of water

Solution 2: commercial buffer solution pH 4.62 (acetate buffer) diluted with the same volume of water The two solutions were separately pumped in at 1 ml/minute and delivered via a tee to a mixing zone. Before the two solutions were combined, samples of the wash liquor (20 μl each) were introduced in segmented form into solution 1 by means of a metering valve and a metering loop. After the two solutions had been mixed, the liquid stream was heated to 70° C. in a heating zone. After passing through a cooling zone (20° C.), the extinction of the liquid was continuously measured at 410 nanometers. The maximum extinction values were regarded as a measure of the glucose concentration and were continuously processed as such by a computer. Calibration was based on aqueous glucose solutions with a concentration of 0.02 to 0.3 g of glucose per liter which were introduced into the analysis circuit several times a day instead of the wash liquor. Sensitivity was automatically corrected by the computer. There was no need in the present case for correction to eliminate the extinction of the glucose-free wash liquor. The analytical data determined by the computer were compared by a microprocessor with the set values programmed therein, the microprocessor actuating the metering valves of the individual compartments and, where necessary, initiating the addition of a corresponding quantity of detergent.

We claim:

1. A process for determining the concentration of a detergent composition in a wash liquor comprising:

(a) preparing a wash liquor containing a detergent composition;

(b) adding a reducing sugar to said wash liquor in an amount proportional to the amount of said a detergent composition present in said wash liquor; and (c) photometrically measuring the content of reducing sugar present in said wash liquor by adding a color-forming reagent to said wash liquor wherein said color-forming reagent reacts with said reducing sugar present in said wash liquor.

2. The process of claim 1 wherein said detergent composition comprises surfactants, builders, redeposition inhibitors, bleaching agents, enzymes, detergency boosters, antimicrobial agents.

3. The process of claim 1 wherein said reducing sugar is glucose.

4. The process of claim 1 wherein from 0.02 to 2.0 grams of said reducing sugar is added per liter of said wash liquor.

5. The process of claim 1 wherein said reducing sugar is present in said detergent composition in an amount of from 1 to 20% by weight, based on the weight of said detergent composition.

6. The process of claim 1 wherein the content of said reducing sugar is measured continuously by flow injection analysis by branching off a stream of said wash liquor.

7. The process of claim 6 wherein said stream of wash liquor has a flow rate of from 0.1 to 2.5 ml per minute.

8. The process of claim 1 wherein said color-forming reagent is an aromatic hydrazine derivative.

9. The process of claim 1 wherein said color-forming reagent is 4-aminobenz hydrazide.

10. The process of claim 1 wherein the result of the measurement is employed for the partial or fully automatic control of detergent dosage in the preparation or regeneration of said wash liquor.

* * * * *